United States Patent
Neun et al.

(10) Patent No.: US 11,864,884 B2
(45) Date of Patent: Jan. 9, 2024

(54) TRACKING REFERENCE FIXATION SUPPORT

(71) Applicant: Brainlab AG, Munich (DE)

(72) Inventors: Tobias Neun, Aschheim (DE); Norman Plassky, Munich (DE); Stefanie Schiele, Munich (DE); Christian Lechner, Tuerkenfeld (DE); Bert Bracke, Vaterstetten (DE)

(73) Assignee: Brainlab AG, Munich (DE)

( * ) Notice: Subject to any disclaimer, the term of this patent is extended or adjusted under 35 U.S.C. 154(b) by 367 days.

(21) Appl. No.: 15/566,962

(22) PCT Filed: May 20, 2016

(86) PCT No.: PCT/EP2016/061447
§ 371 (c)(1),
(2) Date: Oct. 16, 2017

(87) PCT Pub. No.: WO2017/198313
PCT Pub. Date: Nov. 23, 2017

(65) Prior Publication Data
US 2018/0214213 A1 Aug. 2, 2018

(51) Int. Cl.
*A61B 5/11* (2006.01)
*A61B 90/00* (2016.01)
(Continued)

(52) U.S. Cl.
CPC ........... *A61B 5/1114* (2013.01); *A61B 90/39* (2016.02); *A61B 17/00* (2013.01);
(Continued)

(58) Field of Classification Search
CPC .......... A61B 1/0692; A61B 2090/3983; A61B 2034/2072; A61B 5/1114; A61B 90/39;
(Continued)

(56) References Cited

U.S. PATENT DOCUMENTS 2,186,089 A * 1/1940 Baker ............... A44C 5/12
63/11
2,538,265 A * 1/1951 Paston ............ A44C 5/0053
224/176
(Continued)

FOREIGN PATENT DOCUMENTS

DE 20200005573 U1 4/2012
DE 102014104800 A1 10/2015
(Continued)

OTHER PUBLICATIONS

European Patent Office, International Search Report and Written Opinion corresponding to PCT/2016/061447, pp. 1-12, dated Feb. 16, 2017.

*Primary Examiner* — Taylor Morris
(74) *Attorney, Agent, or Firm* — Tucker Ellis LLP

(57) ABSTRACT

A tracking reference fixation support configured to fasten a medical tracking reference to a patient's head, the fixation support comprising an elastically deformable base-plate having a bottom surface, the base-plate being configured to rest via the bottom surface against the surface of a patient's head; an interface-plate providing an interface for rigidly attaching a medical tracking reference to the fixation support; and at least one joint that couples the interface-plate to the base-plate, which allows the base-plate to deform while the interface-plate remains substantially dimensionally stable. The invention further relates to a corresponding tracking reference headband and to a corresponding method of providing a patient's head with a tracking reference.

13 Claims, 5 Drawing Sheets

(51) Int. Cl.
*A61B 17/00* (2006.01)
*A61B 90/50* (2016.01)

(52) U.S. Cl.
CPC ............... *A61B 2017/00862* (2013.01); *A61B 2090/3991* (2016.02); *A61B 2090/502* (2016.02)

(58) Field of Classification Search
CPC .......... A61B 17/00; A61B 2017/00862; A61B 2090/3991; A61B 2090/502; F21V 21/084; A45F 2005/008; A61M 25/02; A61M 2025/026; A61M 2025/0246; A61M 2025/0213; A61M 2025/0253; A61M 2025/0266; A61M 2025/028
USPC ..................................................... 248/346.06
See application file for complete search history.

(56) References Cited

U.S. PATENT DOCUMENTS

| | | | | | |
|---|---|---|---|---|---|
| 3,826,407 | A * | 7/1974 | Keating | ............... | A45D 44/00 221/63 |
| 3,900,026 | A * | 8/1975 | Wagner | ............... | A61M 25/02 128/888 |
| 3,901,226 | A * | 8/1975 | Scardenzan | ............ | A61M 5/00 128/888 |
| 4,060,185 | A * | 11/1977 | Kuroda | ............... | A44C 5/0092 224/176 |
| 4,314,568 | A * | 2/1982 | Loving | ............... | A61M 5/425 604/116 |
| 4,480,639 | A * | 11/1984 | Peterson | ............... | A61M 25/02 128/207.18 |
| 4,561,857 | A * | 12/1985 | Sacks | ............... | A61M 25/02 128/DIG. 6 |
| 4,679,553 | A * | 7/1987 | Proulx | ............... | A61M 25/02 128/846 |
| 4,699,616 | A * | 10/1987 | Nowak | ............... | A61M 25/02 128/DIG. 26 |
| 4,769,010 | A * | 9/1988 | Fenton, Jr. | ............ | A61M 5/46 128/DIG. 26 |
| 4,846,807 | A * | 7/1989 | Safadago | ............ | A61M 5/158 604/179 |
| 4,921,199 | A * | 5/1990 | Villaveces | ............ | A61M 25/02 248/314 |
| 4,974,593 | A * | 12/1990 | Ng | ................. | A61B 5/4362 600/392 |
| 5,000,741 | A * | 3/1991 | Kalt | ................. | A61F 13/023 128/200.26 |
| 5,014,892 | A * | 5/1991 | Copeland | ............... | A45F 5/02 224/242 |
| 5,035,000 | A * | 7/1991 | Matthias | ............... | A41D 27/10 2/123 |
| 5,101,822 | A * | 4/1992 | Kimmel | ............ | A61M 16/0497 128/207.14 |
| 5,238,010 | A * | 8/1993 | Grabenkort | ........ | A61M 25/02 128/846 |
| 5,263,423 | A * | 11/1993 | Anderson | ............... | A45F 5/00 108/43 |
| 5,292,312 | A * | 3/1994 | Delk | ................. | A61M 25/02 128/DIG. 26 |
| 5,305,742 | A * | 4/1994 | Styers | ............... | A61M 16/0488 128/207.17 |
| 5,352,211 | A * | 10/1994 | Merskelly | ............ | A61M 25/02 128/DIG. 26 |
| 5,398,679 | A * | 3/1995 | Freed | .................... | A61M 25/02 128/912 |
| 5,413,562 | A * | 5/1995 | Swauger | ............... | A61M 25/02 128/DIG. 26 |
| 5,470,321 | A * | 11/1995 | Forster | ............... | A61M 25/02 604/174 |
| 5,601,356 | A * | 2/1997 | McWilliams | ............ | A45F 5/00 224/221 |
| 5,693,032 | A * | 12/1997 | Bierman | ............... | A61M 25/02 604/174 |
| 5,722,959 | A * | 3/1998 | Bierman | ............... | A61M 25/02 128/DIG. 26 |
| 5,755,225 | A * | 5/1998 | Hutson | ............... | A61M 16/0488 128/207.14 |
| 5,755,746 | A * | 5/1998 | Lifshey | .................. | A61B 90/39 600/407 |
| 5,812,500 | A * | 9/1998 | Webb, Jr. | ............. | A44C 5/0053 368/10 |
| 5,902,275 | A * | 5/1999 | Dobkin | .................. | A61M 25/02 604/174 |
| 5,916,200 | A * | 6/1999 | Eppley | .................. | A61M 25/02 604/178 |
| 6,071,300 | A * | 6/2000 | Brenneman | ........... | A61M 25/04 606/213 |
| 6,074,368 | A * | 6/2000 | Wright | .................. | A61M 25/02 128/DIG. 26 |
| 6,085,449 | A * | 7/2000 | Tsui | ........................ | A45C 13/42 2/67 |
| 6,132,398 | A * | 10/2000 | Bierman | ............... | A61M 25/02 128/DIG. 26 |
| 6,213,979 | B1 * | 4/2001 | Bierman | ............... | A61M 25/02 128/DIG. 26 |
| 6,228,064 | B1 * | 5/2001 | Abita | .................... | A61M 25/02 604/179 |
| 6,231,548 | B1 * | 5/2001 | Bassett | .................. | A61M 25/02 128/DIG. 26 |
| 6,322,539 | B1 * | 11/2001 | Cook | .................... | A61M 25/02 604/174 |
| 6,361,523 | B1 * | 3/2002 | Bierman | ............... | A61M 25/02 128/DIG. 26 |
| 6,439,530 | B1 * | 8/2002 | Schoenfish | .......... | F16M 11/041 248/346.06 |
| 6,482,175 | B1 * | 11/2002 | Walker | .................. | A61M 25/06 604/115 |
| 6,572,588 | B1 * | 6/2003 | Bierman | ............... | A61M 25/02 128/DIG. 26 |
| 6,579,265 | B1 * | 6/2003 | Kihara | .................... | A61M 1/16 604/174 |
| 6,634,359 | B1 * | 10/2003 | Rudy, Jr. | ........... | A61M 16/0488 128/207.14 |
| 6,695,269 | B1 * | 2/2004 | Anscher | ................. | A45C 13/30 224/269 |
| 7,004,439 | B1 * | 2/2006 | Taylor | ...................... | A42B 3/04 248/548 |
| 7,022,111 | B2 * | 4/2006 | Duplessie | ............. | A61M 25/02 128/DIG. 26 |
| 7,074,208 | B2 * | 7/2006 | Pajunk | .................. | A61M 25/02 128/DIG. 6 |
| 7,284,729 | B2 * | 10/2007 | Walsh | .................... | A61M 25/02 128/877 |
| 7,334,711 | B1 * | 2/2008 | Winters | ..................... | A45F 5/00 224/217 |
| 7,424,110 | B1 * | 9/2008 | Whiten, III | ............... | A45F 5/00 379/454 |
| 7,636,596 | B2 * | 12/2009 | Solar | ...................... | A61B 90/11 606/130 |
| 7,793,892 | B1 * | 9/2010 | Bowen | .................. | A61M 39/08 128/DIG. 26 |
| 7,815,334 | B2 * | 10/2010 | Sherman | ................... | A45F 5/00 224/219 |
| 7,879,013 | B2 * | 2/2011 | Smith | ...................... | A61M 25/02 604/174 |
| 7,981,087 | B2 * | 7/2011 | Gesler, III | ............ | A61M 25/02 604/174 |
| 8,052,649 | B2 * | 11/2011 | Wright | .................. | A61M 25/02 604/174 |
| 8,196,792 | B2 * | 6/2012 | Clifton, Jr. | ................ | A45F 5/00 224/661 |
| 8,197,447 | B2 * | 6/2012 | Wright | .................. | A61M 5/158 128/846 |
| 8,277,420 | B2 * | 10/2012 | Bierman | ............... | A61M 25/02 604/174 |
| 8,359,730 | B2 | 1/2013 | Burg et al. | | |

(56) References Cited

U.S. PATENT DOCUMENTS

| | | | |
|---|---|---|---|
| 8,382,766 B2* | 2/2013 | Warkentine | A61B 17/154 606/88 |
| 8,425,467 B1* | 4/2013 | Haak | A61M 25/02 604/180 |
| 8,708,583 B2* | 4/2014 | Chamberlayne | F16M 11/105 396/423 |
| 8,834,425 B2* | 9/2014 | Bracken | A61L 24/0031 604/174 |
| 8,900,195 B2* | 12/2014 | Delegge | A61J 15/0061 604/174 |
| 8,939,995 B2* | 1/2015 | Lechner | A61L 31/126 606/217 |
| 9,227,039 B1* | 1/2016 | Williams, Sr. | A61M 25/02 |
| 9,314,092 B2* | 4/2016 | Wang | A45F 5/00 |
| 9,526,869 B2* | 12/2016 | Beran | A61M 25/02 |
| 9,615,650 B2* | 4/2017 | Soriano | A45F 5/00 |
| 9,622,557 B1* | 4/2017 | Beavers | A45F 5/00 |
| 9,622,829 B2 | 4/2017 | Vogele | |
| 9,638,354 B1* | 5/2017 | Ogueli | A61M 5/1418 |
| 9,661,912 B1* | 5/2017 | Chung | A45F 5/00 |
| 9,693,622 B1* | 7/2017 | Hackett | A45F 5/00 |
| 9,702,534 B1* | 7/2017 | Brion | F21V 21/084 |
| 9,827,052 B2* | 11/2017 | Fowler | A61B 46/00 |
| 10,156,347 B2* | 12/2018 | Pontano | A42B 3/145 |
| 10,772,523 B2* | 9/2020 | Marcus | A61B 5/053 |
| 11,134,957 B2* | 10/2021 | Harding | A61B 17/135 |
| 2002/0042619 A1* | 4/2002 | Dominguez | A61B 90/14 606/130 |
| 2002/0151871 A1* | 10/2002 | Gaiser | A61B 18/1492 604/528 |
| 2002/0162555 A1* | 11/2002 | West | A61B 1/00154 128/206.29 |
| 2004/0064890 A1* | 4/2004 | Kim | A61N 5/1049 5/601 |
| 2004/0130888 A1* | 7/2004 | Twardawski | B62J 6/02 362/105 |
| 2004/0133078 A1* | 7/2004 | Edoga | A61B 17/02 600/227 |
| 2006/0058738 A1* | 3/2006 | Ponzi | A61M 25/02 604/180 |
| 2006/0064005 A1* | 3/2006 | Triano | A61B 6/04 600/415 |
| 2006/0166720 A1* | 7/2006 | Dixon | H04B 1/385 455/575.6 |
| 2007/0040086 A1* | 2/2007 | Liao | F21L 4/00 248/291.1 |
| 2007/0145149 A1* | 6/2007 | Carnevali | G06F 1/163 235/486 |
| 2008/0041899 A1* | 2/2008 | Park | A45F 5/00 224/271 |
| 2008/0075273 A1* | 3/2008 | Johnson | A45F 5/00 379/426 |
| 2008/0223889 A1* | 9/2008 | Rossell | A44C 5/0007 224/222 |
| 2008/0243085 A1* | 10/2008 | DeStefano | A61M 5/158 604/180 |
| 2009/0254040 A1* | 10/2009 | Bierman | A61M 25/02 604/180 |
| 2010/0010475 A1* | 1/2010 | Teirstein | A61M 25/02 604/528 |
| 2010/0198157 A1* | 8/2010 | Gyrn | A61M 5/14248 604/151 |
| 2010/0234805 A1* | 9/2010 | Kaufmann | A61M 5/14248 604/151 |
| 2010/0327030 A1* | 12/2010 | Yang | A45F 5/00 224/199 |
| 2011/0306934 A1* | 12/2011 | Haider | A61M 25/02 604/174 |
| 2012/0078236 A1 | 3/2012 | Schoepp | |
| 2012/0168571 A1* | 7/2012 | Bond | A61M 25/02 248/70 |
| 2012/0271240 A1* | 10/2012 | Andino | A61M 25/02 604/180 |
| 2012/0316504 A1* | 12/2012 | Kyvik | A61M 25/02 604/180 |
| 2013/0053785 A1* | 2/2013 | Parvatiyar | A61M 25/02 604/174 |
| 2013/0056372 A1* | 3/2013 | Lynch | B65D 75/5877 206/218 |
| 2013/0204094 A1* | 8/2013 | Fiebel | A61B 1/0692 600/249 |
| 2013/0220347 A1* | 8/2013 | Al Otaibi | A61F 15/004 128/888 |
| 2013/0295549 A1* | 11/2013 | Hills | G09B 7/00 434/379 |
| 2014/0142538 A1* | 5/2014 | Hyman | A61M 25/02 604/500 |
| 2014/0155796 A1* | 6/2014 | Yang | A61B 90/50 602/19 |
| 2014/0191095 A1* | 7/2014 | Le Gette | F16M 13/00 248/176.3 |
| 2014/0261513 A1* | 9/2014 | Lammon | A45D 44/00 132/200 |
| 2014/0276658 A1* | 9/2014 | Ward | A61M 25/02 604/541 |
| 2014/0324024 A1* | 10/2014 | Tejani | A61M 25/02 604/178 |
| 2015/0038912 A1* | 2/2015 | Karim | A61M 25/02 604/178 |
| 2015/0057618 A1* | 2/2015 | Escobedo | A61M 25/02 604/180 |
| 2015/0150360 A1* | 6/2015 | Soriano | A45F 5/00 224/222 |
| 2015/0182009 A1* | 7/2015 | Whang | A45F 5/00 224/222 |
| 2015/0223590 A1* | 8/2015 | Arias-Tabima | A45F 5/021 224/195 |
| 2015/0282735 A1 | 10/2015 | Rossner | |
| 2015/0288407 A1* | 10/2015 | Hernandez | H04B 1/3888 224/267 |
| 2015/0297867 A1* | 10/2015 | Howell | A61M 25/02 604/174 |
| 2016/0058163 A1* | 3/2016 | Lee | A45F 5/00 224/267 |
| 2016/0106508 A1* | 4/2016 | Lathrop | A61B 90/14 606/130 |
| 2016/0174674 A1* | 6/2016 | Oberpriller | A45F 5/021 224/222 |
| 2016/0207228 A1* | 7/2016 | Ferguson | B29C 39/10 |
| 2016/0249990 A1* | 9/2016 | Glozman | A61B 90/11 606/130 |
| 2016/0367789 A1* | 12/2016 | Beran | A61M 25/02 |
| 2017/0086813 A1* | 3/2017 | Hess | A61B 17/3403 |
| 2017/0086941 A1* | 3/2017 | Marti | A61B 34/20 |
| 2017/0189647 A1* | 7/2017 | Elsamahy | A61M 25/02 |
| 2017/0209222 A1 | 7/2017 | Gassner et al. | |
| 2017/0303859 A1* | 10/2017 | Robertson | A61B 5/6819 |
| 2017/0333154 A1* | 11/2017 | LeBeau | A61B 90/39 |
| 2018/0177982 A1* | 6/2018 | Albany | A61M 25/02 |
| 2018/0264232 A1* | 9/2018 | Beran | A61M 25/02 |
| 2019/0015636 A1* | 1/2019 | Robinson | A61M 25/02 |
| 2019/0116966 A1* | 4/2019 | Gregory | A45F 5/021 |
| 2019/0117939 A1* | 4/2019 | Price | A61M 25/02 |
| 2019/0125397 A1* | 5/2019 | Arnold | A61B 90/50 |
| 2019/0160262 A1* | 5/2019 | Jones | A61M 25/02 |
| 2019/0175877 A1* | 6/2019 | Anzalone | A61M 25/02 |
| 2019/0282263 A1* | 9/2019 | Kincaid | A61B 34/20 |
| 2019/0314112 A1* | 10/2019 | Wellborn | A61B 90/39 |
| 2019/0388303 A1* | 12/2019 | Sharaiha | A61J 15/0061 |
| 2019/0390845 A1* | 12/2019 | Ljunggren | F21V 21/145 |
| 2020/0078562 A1* | 3/2020 | Chambers | A61M 25/02 |
| 2020/0206468 A1* | 7/2020 | Olson | A61M 25/02 |
| 2020/0254221 A1* | 8/2020 | Burkin | A61M 27/00 |
| 2021/0113815 A1* | 4/2021 | Karim | A61M 25/02 |
| 2022/0304888 A1* | 9/2022 | Faii Ong | A61H 23/0254 |

(56) References Cited

U.S. PATENT DOCUMENTS

FOREIGN PATENT DOCUMENTS

| | | | |
|---|---|---|---|
| EP | 2345384 A1 | 7/2011 | |
| FR | 2998471 A3 * | 5/2014 | ............ A61B 90/39 |
| WO | 0224096 A1 | 3/2002 | |

* cited by examiner

TRACKING REFERENCE FIXATION SUPPORT

CROSS-REFERENCE TO RELATED APPLICATIONS

This application is a national phase application of International Application No. PCT/EP2016/061477 filed May 20, 2016, and published in the English language.

BACKGROUND

The present invention relates to a fixation support for a tracking reference as used during medical or surgical procedures which require the spatial position of the patient's head to be known. The present invention further relates to a corresponding tracking reference headband comprising such fixation support and to a corresponding method of providing a patient's head with a medical tracking reference.

Non-invasive solutions for providing a patient's head with a tracking reference are known, including a mounting structure to which a tracking reference can be attached and which is strapped to the patient's forehead via a strap-like headband. In order to prevent the mount together with the tracking reference to shift with respect to the head over time, leading to faulty tracking data, the headband is firmly tightened. This however causes the mount to apply concentrated pressure on the patient's forehead which may even lead to skin injuries. Loosening the strap by even a small amount however increases the risk for the tracking reference to shift.

It is the object of the present invention to provide a fixation support that allows a tracking reference to be safely attached to a patient's head without the risk of damaging tissue.

This object is solved by the subject matter of independent claims 1, 13 and 15.

SUMMARY

The tracking reference fixation support according to the present invention, which is configured to fasten a medical tracking reference to a patient's head, comprises:
- an elastically deformable base-plate having a bottom surface, the base-plate being configured to rest via the bottom surface against the surface of a patient's head;
- an interface-plate providing an interface for rigidly attaching a medical tracking reference to the fixation support;
- at least one joint that couples the interface-plate to the base-plate, which allows the base-plate to deform while the interface-plate remains substantially dimensionally stable.

In other words, the inventive fixation support comprises two structures, namely a base-structure and an interface-structure, which are coupled to each other via one or more joints, such that the base-structure can easily adapt to the three-dimensional shape of the patient's head, whereas the interface-structure maintains its shape and therefore provides a safe support for the tracking reference. With the base-structure being easily deformable, the contacting surface between the fixation support and the patient's head increases as soon as the support is pressed onto the head, thereby avoiding that discrete regions of the patient's head are overly pressurized.

As compared with the base-structure, the interface-structure may be also relatively stiff to provide an adequate mounting for maintaining the spatial location and orientation of a tracking reference with respect to the patient's head the fixation support is attached to. With the base-structure being relatively flexible and the interface-structure being relatively stiff, the one or more coupling joints or hinges have to sufficiently brace the interface-structure to the base-structure.

In a further embodiment, the interface-plate is spaced from the base-plate in a direction substantially perpendicular to the bottom surface. Spacing the interface-structure and the bottom-structure from each other will "decouple" the interface-plate from the base-plate even more, with the joints or hinges remaining as the only connecting link between those structures. In this case, a plurality of joints or hinges, for example two, three or four joints or hinges may help in bracing the interface-plate to the base-plate.

In a further embodiment, the interface-plate is connected to the base-plate via at least one film-joint, particularly via at least one pair of film-joints disposed on opposite sides of the interface-plate, wherein the joint(s) extend(s) in a direction substantially parallel to a bending axis of the base-plate. In this embodiment, at least one joint is integrally formed with at least one of the base-plate and the interface-plate. This however does not mean that the base-plate is made from the same material as the interface-plate, since one of the plates including the at least one film-joint may be mounted to the other one of the plates. However, such film-joints provide the possibility to integrally form the interface-plate with the base-plate.

Further, the at least one joint or hinge may be configured or oriented with respect to the base-plate in such a manner that it predominantly allows for a rotational motion around an axis which is substantially parallel to an expected bending axis of the base-plate.

Further, the base-plate may have a preferred bending axis. On the other hand, the base-plate may be also deformable over substantially the whole bottom surface that rests on the patient's head.

In order to decrease the amount of deformation necessary to perfectly adapt to the curved shape of the patient's head, the base-plate may be already "pre-shaped" by having a curved surface in at least one, particularly in two dimensions.

In a further embodiment, the interface-plate and the base-plate are formed as separate parts which may consequently be made from different materials. In that case, a relatively flexible material may be chosen for the base-plate, wherein a relatively rigid material may be chosen for the interface-plate. Further, the interface-plate and the base-plate may be detachably coupled to each other, particularly via a snap-in-connection. However, as already mentioned above, the interface-plate, the base-plate and the at least one joint may be integrally formed. In order to increase visibility of any anatomical structures lying underneath the fixation support, at least the base-plate may be made from a transparent material.

For further increasing flexibility of the base-plate, the base-plate may have at least one bending section having a reduced resistance against bending. This may be achieved by providing the base-plate with at least one gap and/or at least one section having a reduced material thickness. Such flexibility-increasing bending sections, may be provided for at least one, preferably for two perpendicular directions, such that the base-plate perfectly adapts to the three-dimensional shape of the patient's head.

For adequately straining the fixation support in its intended position to the patient's head, the base-plate may have at least one fastening section configured to be engaged by a fastening member, particularly by a strap-like fastening member. This fastening section may take the shape of an elongated through-hole formed in the base-plate. Preferably, the base-plate may be provided with two of such fastening sections which further may be disposed on opposite's sites of the base-plate.

A further aspect of the present invention relates to a tracking reference headband comprising a fixation support as described above an at least one fastening member configured to reach around a patient's head and to fasten the fixation support to the patient's head by being tightened. As a further measure to maintain the position of the fixation support together with the tracking reference with respect to the patient's head, the bottom surface of the base-plate may be provided with an adhesive configured to adhere to the patient's skin. Such adhesive may be provided by a soft adhesive pad, particularly a foam pad, that further increases the wearing comfort of the fixation support.

A further aspect of the present invention relates to a method for providing a patient's head with a medical tracking reference, comprising the steps of:
- providing a tracking reference headband as described above;
- fixing the headband to the patient's head by adhering the fixation support to the patient's forehead and tightening the at least one fastening member; and
- attaching the medical tracking reference to the fixation support via the interface.

BRIEF DESCRIPTION OF THE DRAWINGS

In the following, the invention is described with reference to the enclosed Figures which represent preferred embodiments of the invention. The scope of the invention is however not limited to the specific features disclosed in the Figures, which show.

DETAILED DESCRIPTION OF THE INVENTION

Figure 1:
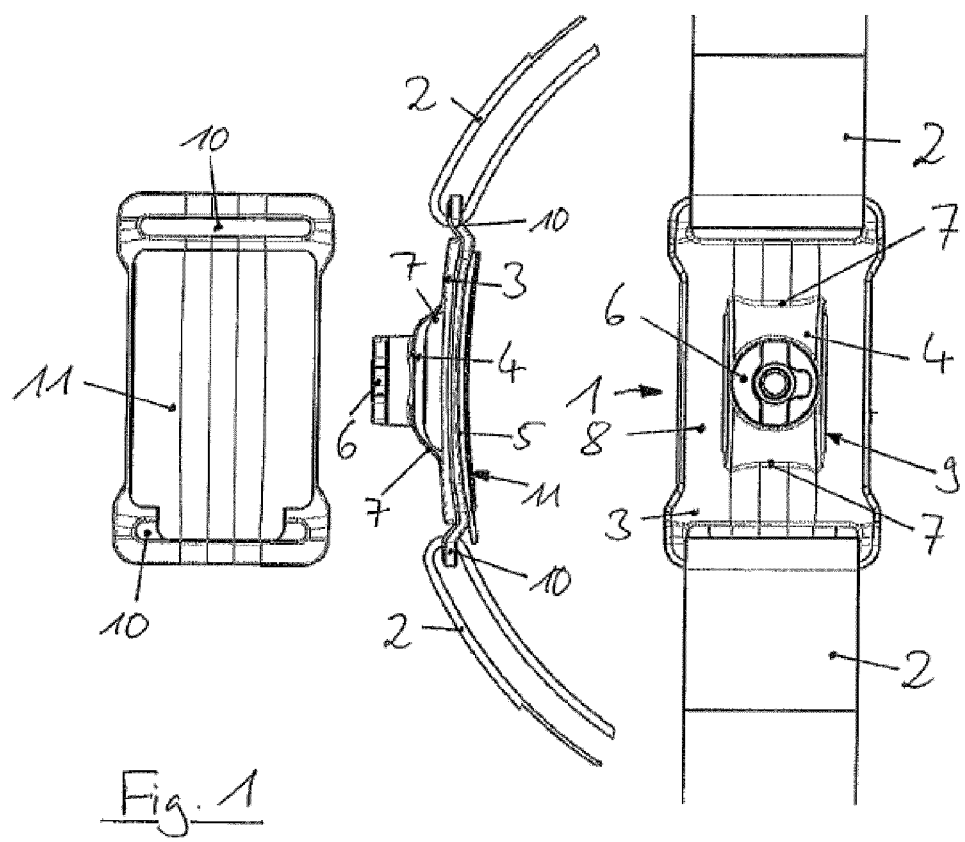
FIG. 1 a tracking reference headband comprising a first embodiment of the fixation support according to the present invention.

FIG. 1 shows a tracking reference headband according to the present invention that comprises a fixation support 1 at a central location. On both lateral ends of the fixation support 1, elongated through-holes are provided as fastening-sections 10, which allow an elastic strap 2 to engage the fixation support so as to retain the fixation support 1 in a desired position on a patient's forehead. For that purpose, the bottom surface 5 of the fixation support 1 is further provided with an adhesive foam pad 11 that will stick on the patient's skin.

In order to increase the wearing comfort of the headband, the fixation support 1 is divided into two plate-shaped sections, namely a base-plate 3 and an interface-plate 4. It will become apparent from the central drawing in FIG. 1 that the base-plate 3 will easily flex as soon as tension is applied via the fastening member 2, such that the curvature of the base-plate 3 conforms to the curvature of the surface of the patient's head the support is applied to. Since the interface-plate 4 is spaced from the base-plate 3 and is connected to the base-plate 3 via the two film-joints 7 only, flexibility of the base-plate 3 is not compromised by the interface-plate 4. Further, the film-joints 7 provide sufficient support for the interface-plate 4 to prevent the interface-plate 4 from deflecting either around an axis which is parallel to the extension of the film-joints 7, and around an axis which is perpendicular to the extension of the film-joints 7. Consequently, any medical tracking reference attached to the fixation support 1 via the interface 6 will maintain its spatial location and orientation with respect to the patient's head, even though the base-plates 3 flexibility and therefore the wearing comfort of the fixation support 1 is significantly increased.

For flexibility reasons, the base-plate 3 is, as shown by the right depiction in FIG. 1, provided with a cut-out 9 underneath the interface-plate 4, leaving two bending sections 8 which flank the interface-section 4.

Figure 2:
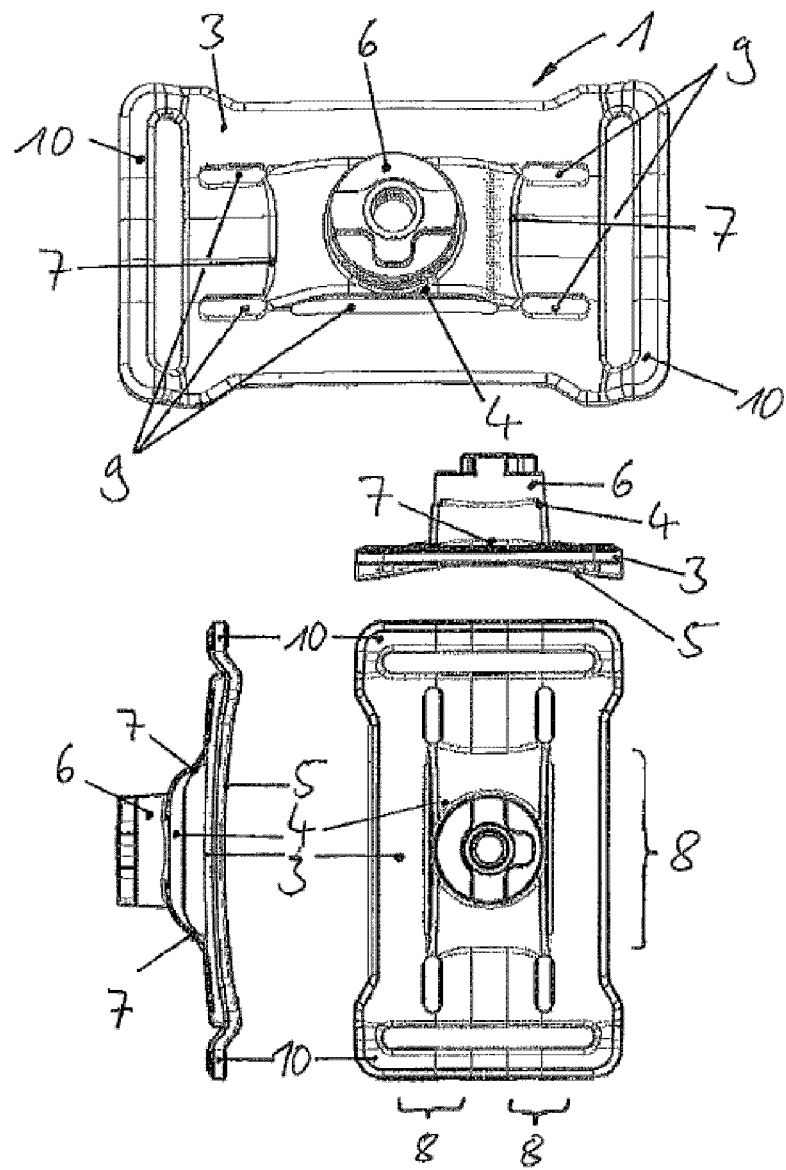
FIG. 2 a second embodiment of the fixation support.

FIG. 2 shows a further preferred embodiment of the fixation support, differing from the fixation support 1 shown in FIG. 1 only in that additional cut-outs 9 are provided in the base-plate 3, which allow the base-plate 3 to flex more easily in a direction perpendicular to the extension of the film-joints 7. While the central cut-out 9 underneath the interface-section 4 causes a reduced bending resistance in a horizontal direction, the four additional cut-outs 9 at the film-joints 7 cause a reduced bending resistance in a vertical direction by leaving two additional sections 8 that extend right next to the interface-section 4 in a top-view onto the fixation support 1.

As FIG. 2 shows, the base-plate 3 has a curved basic shape not only in a horizontal direction which is perpendicular to the extension of the film-joints 7, but also has a curved shape in a vertical direction parallel to the extension of film-joints 7.

Figure 3:
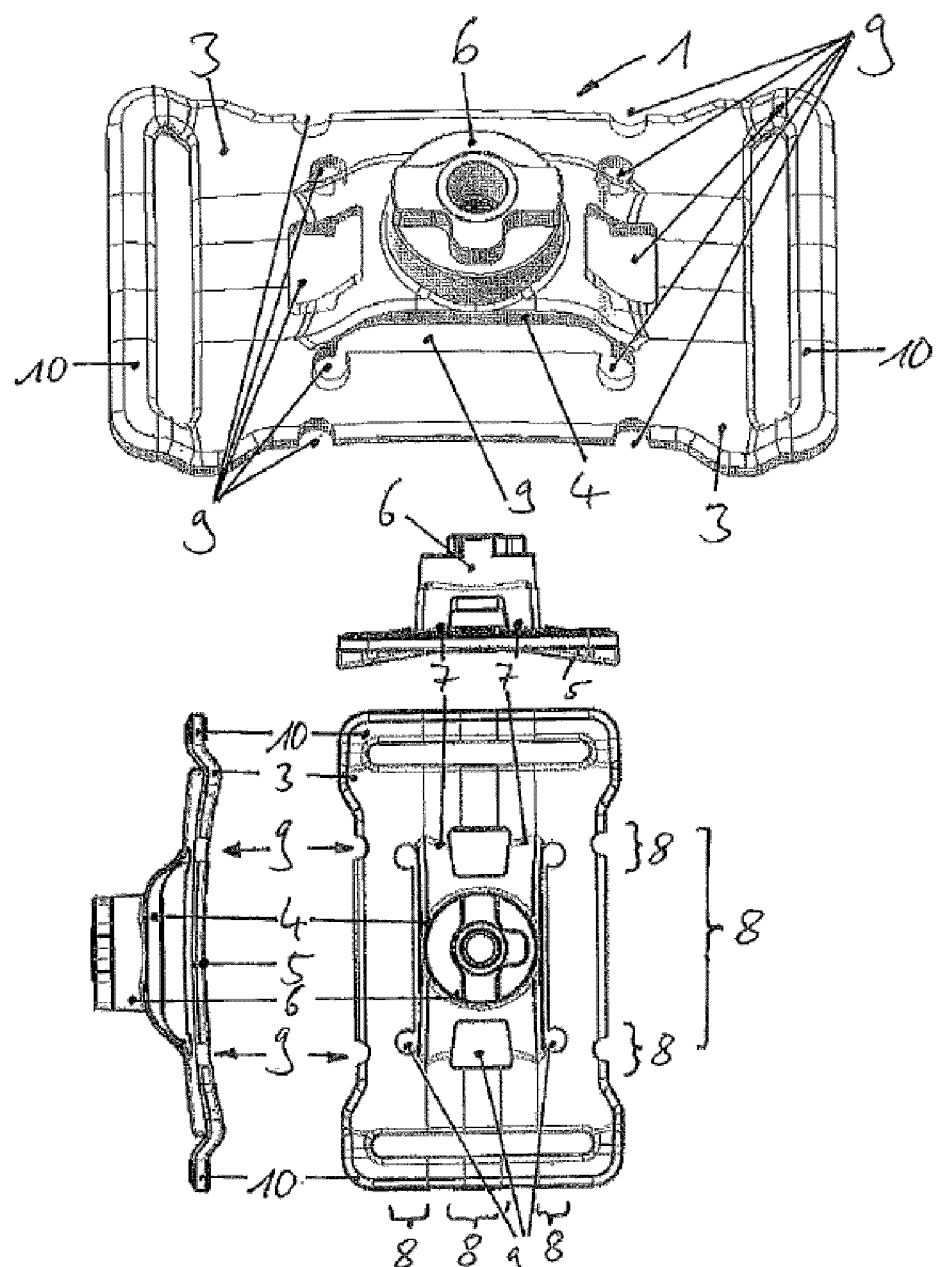
FIG. 3 a third embodiment of the fixation support.

FIG. 3 shows a further embodiment of the inventive fixation support, having even more cut-outs 9 in the base-plate 3 for reducing the resistance against bending even more within the bending sections 8. In particular, each of the film-joints 7 is divided by a cut-out 9, allowing the base-plate 3 to bend underneath the interface-plate 4 in a direction perpendicular to the extension of the film-joints 7.

All of the fixation supports 1 shown in FIGS. 1 to 3 are integrally formed as a single element. In the alternative, the base-plate 3 and the interface-plate 4 may be formed as separate parts as shown in FIGS. 4 and 5.

Figure 4:
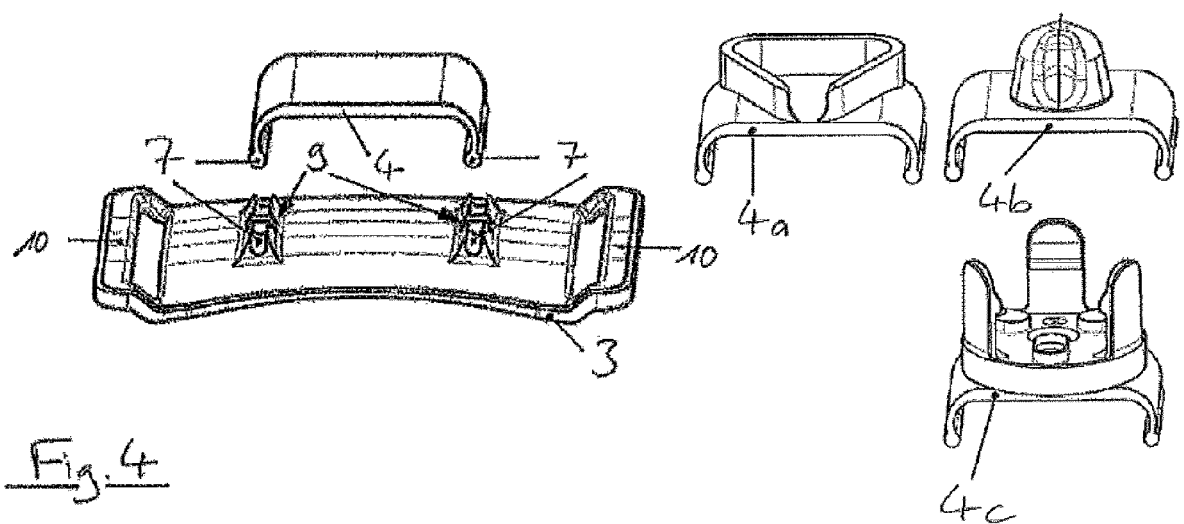
FIG. 4 fourth embodiment of the fixation support.

FIG. 4 shows a two-part-fixation support 1. The joints 7 on both ends of the interface-plate 4 act as a snap-in-interface, that not only allow the interface-plate 4 to be snapped onto the base-plate 3, but also allows the base-plate 3 to bend under the interface-plate 4. Any variation of the distance between the joints 7 caused by bending the base-plate 3 will be compensated for by the flexible extensions of the interface-plate 4, extending downwards towards the joints 7.

Figure 5:
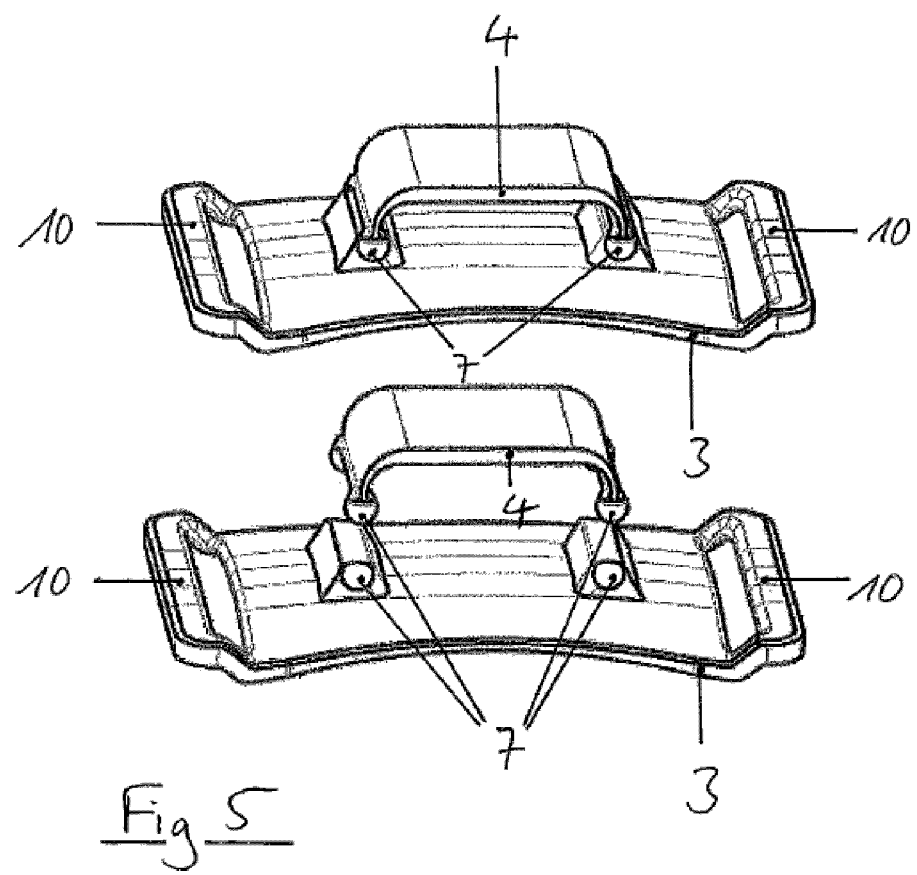
FIG. 5 a fifth embodiment of the fixation support.

While the joints 7 shown in FIG. 4 allow for a relative motion between the base-plate 3 and the interface-plate 4 around a single axis, the ball-joints 7 of the embodiment shown in FIG. 5 also allow for a relative motion around a further axis. Again, the four ball-joints 7 provide a snap-in-fit allowing the interface-plate 4 to be detachably mounted onto the base-plate 3. The ball-joints 7 allow the base-plate 3 to bend under the interface-plate 4 in two dimensions, as the ball-joints 7 allow a rotation about a second axis.

A further advantage of an interface-plate 4 and a base-plate 3 being provided as separate parts, as shown for example in FIGS. 4 and 5, becomes apparent by looking at FIG. 4: Since the interface-plate 4 is detachable from the base-plate 3, a plurality of interchangeable interface-plates 4a, 4b, 4c may be provided, with different kinds of interfaces for different kinds of tracking markers. Such a "system" comprising a base-plate 3 and different kinds of interface-plates 4 offers the possibility to utilize one and the same base-plate 3 in conjunction with different kinds of tracking-systems. It is even conceivable to use such system for replacing one kind of tracking marker by another kind of tracking marker, with the base-plate 3 remaining attached to the patient's head. Further, the interchangeable interface-plates 4a, 4b, 4c may be configured to position the respective tracking markers in positions that are "calibrated" among each other, such that a recalibration is unnecessary after replacing one tracking marker together with a respective interface-plate 4 by another one.

The invention claimed is:

1. A tracking reference fixation support configured to fasten a medical tracking reference to a head of a patient, the fixation support comprising:
   an elastically deformable base-plate having a bottom surface, wherein the base-plate is configured to rest via the bottom surface against a surface of the head of the patient;
   a stiff interface-plate which provides an interface at a location spaced from the base-plate in a direction substantially perpendicular to the bottom surface, the interface being configured to rigidly connect to the medical tracking reference, wherein the stiff interface-plate is formed as a single element that connects between the interface and the elastically deformable base-plate, wherein the stiff interface-plate and the elastically deformable base-plate connect to each other at a first hinge section having a first bending axis and a second hinge having a second bending axis extending parallel to the first bending axis, thereby allowing the base-plate to flex below the interface plate and about an axis extending parallel to the first bending axis and the second bending axis while the interface-plate remains substantially dimensionally stable, and
   a fastening member which is adapted to engage a pair of fastening sections disposed on opposite sides of the base-plate, the fastening member being further adapted to reach around the head of the patient so as to fasten the fixation support to the head of the patient by being tightened.

2. The fixation support according to claim 1, wherein the pair of hinges is a pair of film hinges and the interface-plate is connected to the base-plate via the pair of film hinges.

3. The fixation support according to claim 2, wherein the film hinges are disposed on opposite sides of the interface-plate, and wherein the film hinges extend in a direction substantially parallel to a bending axis of the base-plate.

4. The fixation support according to claim 1, wherein the base-plate is deformable over substantially the whole bottom surface.

5. The fixation support according to claim 1, wherein the bottom surface is curved in a first dimension.

6. The fixation support according to claim 5, wherein the bottom surface is curved in a second dimension.

7. The fixation support according to claim 1, wherein the interface-plate is a separate part from the base-plate, and/or wherein the base-plate is made from a different material than the interface plate.

8. The fixation support according to claim 7, wherein the interface-plate and base-plate are releasably attached to each other.

9. The fixation support according to claim 1, wherein the interface-plate is integrally formed with the base-plate and the pair of hinges are made from a transparent material.

10. The fixation support according to claim 1, wherein the base-plate has at least one bending section.

11. The fixation support according to claim 10, wherein the at least one bending section of the base-plate includes a gap.

12. The fixation support according to claim 10, wherein the at least one bending section of the base-plate includes a reduced material thickness compared to at least one remaining section of the base-plate in a cross-section perpendicular to the corresponding bending axis/axes.

13. The fixation support according to claim 1, wherein the base-plate is elastically deformable in two perpendicular directions.

* * * * *

UNITED STATES PATENT AND TRADEMARK OFFICE
CERTIFICATE OF CORRECTION

| | | |
|---|---|---|
| PATENT NO. | : 11,864,884 B2 | |
| APPLICATION NO. | : 15/566962 | |
| DATED | : January 9, 2024 | |
| INVENTOR(S) | : Tobias Neun et al. | |

It is certified that error appears in the above-identified patent and that said Letters Patent is hereby corrected as shown below:

On the Title Page

Item (72) Inventor Stefanie Schiele should be indicated as Stephanie Schiele

Signed and Sealed this
Thirteenth Day of February, 2024

Katherine Kelly Vidal
*Director of the United States Patent and Trademark Office*